United States Patent
Ikemoto et al.

(10) Patent No.: US 6,977,306 B2
(45) Date of Patent: Dec. 20, 2005

(54) CITALOPRAM HYDROBROMIDE CRYSTAL AND METHOD FOR CRYSTALLIZATION THEREOF

(75) Inventors: Tetsuya Ikemoto, Osaka (JP); Nobuhiro Arai, Osaka (JP); Masami Igi, Osaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 434 days.

(21) Appl. No.: 09/824,447

(22) Filed: Apr. 2, 2001

(65) Prior Publication Data

US 2001/0049450 A1 Dec. 6, 2001

(30) Foreign Application Priority Data

May 2, 2000 (JP) ......................................... 2000/133995

(51) Int. Cl.[7] ..................... C07D 307/78; A61K 31/343
(52) U.S. Cl. ........................................ 549/467; 514/469
(58) Field of Search ................................ 549/467, 469; 514/469

(56) References Cited

U.S. PATENT DOCUMENTS

| 4,136,193 A | 1/1979 | Bøgesø et al. |
| 4,650,884 A | 3/1987 | Bogeso |
| 2003/0109577 A1 | 6/2003 | Liljegren et al. |

| 2003/0232881 A1 | 12/2003 | Liljegren et al. |

FOREIGN PATENT DOCUMENTS

| DE | 200 07 303 U1 | 7/2000 |
| GB | 2 357 762 A | 7/2001 |
| WO | WO 00/23431 | 4/2000 |

OTHER PUBLICATIONS

Vilarrasa, *Eunibar*, Editorial Universitaria de Barcelona, pp. 63–64 (Dec. 1975).
Carré, "Précis de Technologie et de Chimie Industrielle," vol. 1, pp. 319–320 (Librairie J.–B. Bailliére et Fils, Paris, France, 1938).
U.S. Appl. No. 09/794,755, Petersen et al., filed Feb. 26, 2001, date of publication, Jan. 10, 2002.
"3.1.1 Crystallization by Control of Temperature Change," *Organic Crystals Formation Handbook*, pp. 34–35 (2000).

*Primary Examiner*—Charanjit S. Aulakh
(74) *Attorney, Agent, or Firm*—Leydig, Voit & Mayer, Ltd.

(57) ABSTRACT

According to the present invention, citalopram hydrobromide dissolved in a solvent containing at least one member selected from the group consisting of alcohol having 1–3 carbon atoms, water and acetone is crystallized or recrystallized while controlling the cooling rate, thereby to 1) provide an industrial method for crystallizing citalopram hydrobromide, which enables easy control of the crystal characteristics, such as particle size, particle size distribution and aspect ratio and the like of the crystal, and 2) provide citalopram hydrobromide crystal having crystal characteristics useful as a pharmaceutical bulk.

17 Claims, 17 Drawing Sheets

CITALOPRAM HYDROBROMIDE CRYSTAL AND METHOD FOR CRYSTALLIZATION THEREOF

TECHNICAL FIELD OF THE INVENTION

The present invention relates to a method for crystallizing citalopram hydrobromide useful as an antidepressant and citalopram hydrobromide having specific crystal properties.

BACKGROUND OF THE INVENTION

Citalopram hydrobromide is useful as an antidepressant. When it is used as a pharmaceutical bulk for the preparation of a pharmaceutical agent, particle size, particle size distribution and aspect ratio of the crystal are the important crystal characteristics. However, there is no teaching as to what crystal characteristics of citalopram hydrobromide are required as a beneficial pharmaceutical bulk, or a method for achieving such beneficial crystal characteristics.

According to U.S. Pat. No. 4,650,884, for example, a method for crystallizing citalopram hydrobromide comprises, crystallization in a single solvent of acetone, first recrystallization in a single solvent of water, second recrystallization in a mixed solvent of methanol and isopropyl alcohol, and third recrystallization in a mixed solvent of methanol, acetone and hexane. This method aims at purification of citalopram crystals but not at controlling particle size, particle size distribution or aspect ratio of crystals, not to mention a method for controlling these.

When citalopram hydrobromide is crystallized according to the method described in this publication, fine crystals having a particle size of less than 5 μm are formed in a large amount (41.9% of the total amount). When fine crystals are contained in a large amount, filtering performance after crystallization for medicament production is degraded. In addition, the fine particles scatter and the workers are exposed thereto during production of pharmaceutical preparations, which is an unpreferable aspect as a pharmaceutical bulk.

When citalopram hydrobromide is crystallized according to the method described in this publication, crystals having a smaller average aspect ratio of less than 2 are produced. Such crystals cause problems such as poor filtering performance after crystallization for the preparation of a pharmaceutical agent and poor fluidity when crystals are being taken out, which is not preferable as a pharmaceutical bulk.

It is therefore an object of the present invention to provide
(1) a method for industrially crystallizing citalopram hydrobromide, which method affords easy control of crystal characteristics, such as particle size, particle size distribution and aspect ratio of the crystals, and
(2) citalopram hydrobromide crystals having crystal characteristics useful as a pharmaceutical bulk.

SUMMARY OF THE INVENTION

Such object can be achieved by the present invention. According to the present invention, citalopram hydrobromide dissolved in a specific solvent is crystallized or recrystallized while controlling the cooling rate, thereby to control the particle size, particle size distribution and aspect ratio of citalopram hydrobromide crystals. It has been also found that citalopram hydrobromide crystals containing crystals having a particle size of less than of 5 μm in a proportion of 35% at most and citalopram hydrobromide crystals having an average aspect ratio of not less than 4.5 and not more than 6.0, which are obtained by this method, are advantageous as a pharmaceutical bulk.

Accordingly, the present invention provides the following.

(1) Citalopram hydrobromide crystals containing crystals having a particle size of less than 5 μm in a proportion of 35% at most.
(2) Citalopram hydrobromide crystals containing crystals having a particle size of less than 5 μm in a proportion of 35% at most, and containing crystals having a particle size of not less than 20 μm in a proportion of not less than 10%, or having an average aspect ratio of not less than 2.0 and not more than 9.0, or having an average aspect ratio of not less than 2.5 and less than 4.5, or having an average aspect ratio of not less than 4.5 and not more than 6.0.
(3) Citalopram hydrobromide crystals having an average aspect ratio of not less than 2.0 and not more than 9.0.
(4) Citalopram hydrobromide crystals having an average aspect ratio of not less than 2.5 and less than 4.5.
(5) Citalopram hydrobromide crystals having an average aspect ratio of not less than 4.5 and not more than 6.0.
(6) A method for crystallizing citalopram hydrobromide, which comprises the steps of
(A1) dissolving, by heating, citalopram hydrobromide in a solvent containing at least one member selected from the group consisting of alcohol having 1 to 3 carbon atoms, water and acetone and
(B1) cooling the resulting product to achieve crystallization, while controlling the cooling rate.
(7) A method for crystallizing citalopram hydrobromide, which comprises the steps of
(A2) dissolving, by heating, citalopram hydrobromide in a solvent containing at least one member selected from the group consisting of alcohol having 1 to 3 carbon atoms, water and acetone,
(B2) cooling the obtained solution to achieve crystallization,
(C2) dissolving a part of the obtained crystals by heating, and
(D2) recrystallizing the crystals while controlling the cooling rate.

A preferable mode of the above-mentioned (6) includes
(6-1) controlling the cooling rate within the temperature range of 0° C.–80° C.,
(6-2) controlling the average cooling rate within the temperature range of 20° C.–40° C. to not less than 30° C./hour and not more than 60° C./hour,
(6-3) controlling the average cooling rate within the temperature range of 20° C.–40° C. to not less than 0.5° C./hour and less than 30° C./hour, and
(6-4) cooling the solution obtained in (A1) to a temperature range of not less than 30° C. and less than 48° C. and adding a seed crystal of citalopram hydrobromide to achieve crystallization.

A preferable mode of the above-mentioned (7) includes
(7-1) cooling to the temperature range of not less than 30° C. and less than 48° C. in (B2),
(7-2) after cooling to the temperature range of not less than 30° C. and less than 48° C., adding a seed crystal of citalopram hydrobromide to achieve crystallization in (B2),
(7-3) heating to the temperature range of not less than 48° C. and not more than 60° C. to dissolve a part of the crystal in (C2),
(7-4) controlling the average cooling rate in the temperature range of from (heating temperature in (C2)) to (this heating temperature—30° C.) to not less than 30° C./hour and not more than 90° C./hour in (D2), and (7-5) controlling the average cooling rate in the temperature range of from (heating temperature in (C2)) to (this heating temperature—30° C.) to not less than 1° C./hour and less than 30° C./hour in (D2).

DETAILED DESCRIPTION OF THE INVENTION

Figure 1:
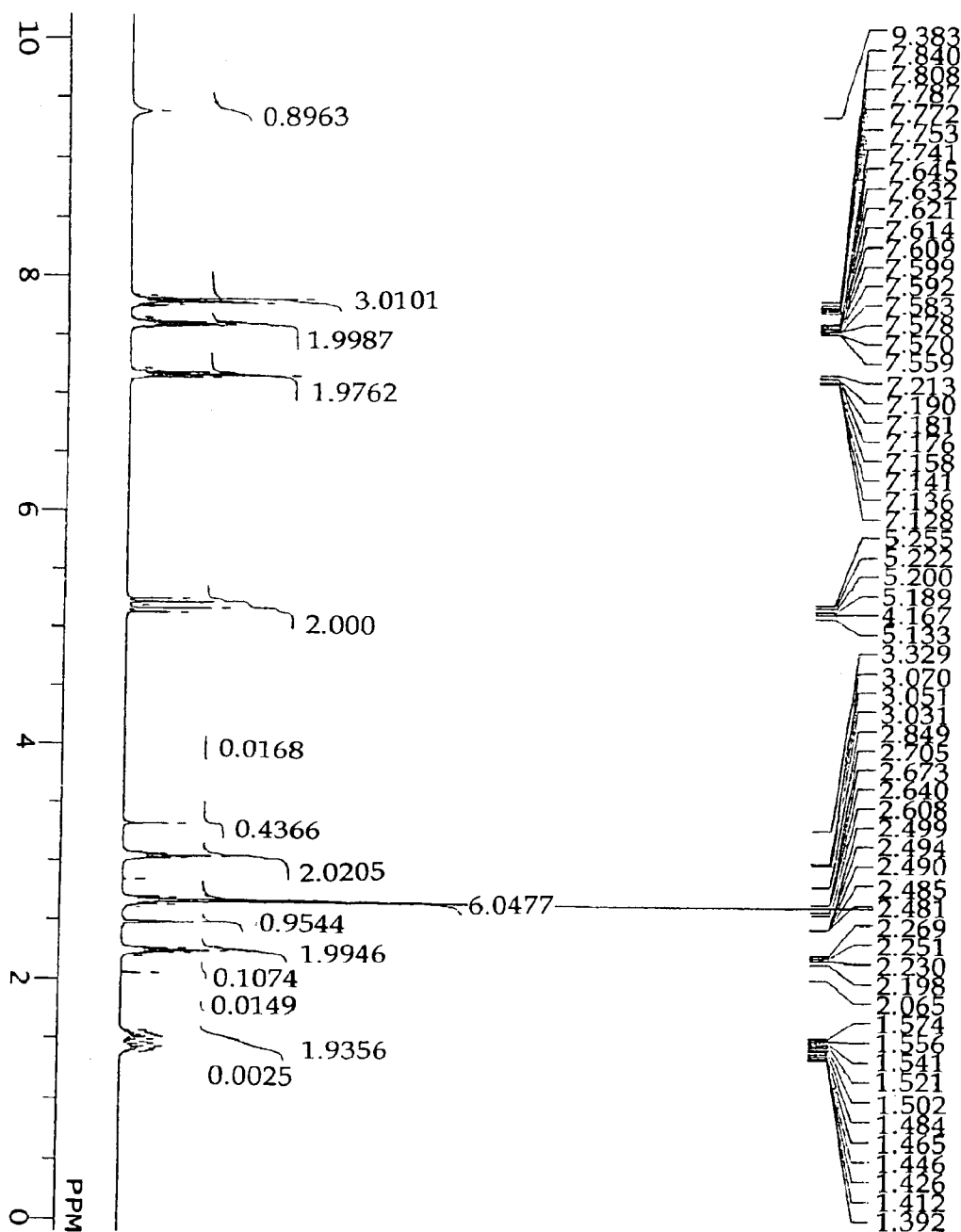
FIG. 1 shows $^1$H-NMR of the compound obtained in Reference Example 1.

The present invention is explained in detail in the following.

The average particle size in the present invention is an average diameter upon conversion of the volume of the crystal particles into sphere.

The average aspect ratio in the present invention is an average value of the major axis/minor axis of crystal particles.

According to the present invention, crystal characteristics such as particle size, particle size distribution and aspect ratio of the crystals can be controlled easily. As the industrial method for crystallizing citalopram hydrobromide includes the following methods.

Method 1

A first method for crystallizing citalopram hydrobromide in the present invention includes (A1) dissolving citalopram hydrobromide in a specific solvent, and (B1) crystallization by cooling the resulting solution while controlling a cooling rate (hereinafter this method is to be referred to as Method 1). The crystals obtained according to Method 1 generally show a smooth cone-shaped particle size distribution.

In the following, the steps (A1) and (B1) are explained in detail. In each step, it is preferable that the particles be stirred at 10 rpm–250 rpm, particularly at 50 rpm–220 rpm, so that the temperature of the system as a whole can be uniform and the crystals after stirring will not have a smaller aspect ratio.

According to Method 1, the cooling rate of the solution within the specific temperature range should be regulated to control the crystal characteristics. That is, the present inventors have found that the cooling rate of the solution within the temperature range of preferably 0° C.–80° C., particularly 20° C.–40° C., in (B1) affects the crystal particle size of citalopram hydrobromide. For example, the crystals obtained when the average cooling rate of the solution within the temperature range of 20° C.–40° C. is controlled to not less than 0.5° C./hour and less than 30° C./hour contain crystals having a particle size of less than 5 μm in a proportion of 35% at most, and have an average particle size of about 10 μm–20 μm, and that the crystals obtained when it is controlled to not less than 30° C./hour and not more than 60° C./hour contain crystals having a particle size of less than 5 μm in a proportion of 35% at most, and have an average particle size of about 7 μm–15 μm. Cooling within the above-mentioned temperature range is preferably conducted such that the cooling rate becomes almost constant.

A next important process for controlling the crystal characteristics is the addition of seed crystal in (B1) in the specific temperature range. Addition of a seed crystal for crystallization of a compound is a known preferable method for precipitating crystals, as demonstrated in U.S. Pat. No. 4,650,884 with regard to citalopram hydrobromide. In this publication, a seed crystal is added when the cooling temperature is 20° C. By reproductive crystallization according to this method by the present inventors, it was revealed that suitable growth of the precipitated crystals was not achieved, with a considerable amount of fine crystals having a particle size of less than 5 μm. When fine crystals are contained in a great amount, filterability after crystallization for the preparation of a pharmaceutical bulk becomes poor, and the fine particles scatter, to which particles the workers are exposed during production of pharmaceutical preparations.

The present inventors have also found that, in (B1), cooling to the temperature range of preferably not less than 30° C. and less than 48° C., more preferably not less than 40° C. and less than 48° C., followed by addition of a seed crystal to allow for crystallization, results in precipitation of crystals suitably grown. Thus, the particle size of the crystals can be controlled well, and generation of fine crystals having a particle size of less than 5 μm can be further inhibited by this method.

When the temperature, at which a seed crystal is added, is less than 30° C., crystallization occurs at once and fine crystals tend to increase. When it is not less than 48° C., the seed crystal tends to dissolve easily, and the effect of the addition of the seed crystal becomes low. The amount of the seed crystal added is not subject to any particular limitation, but it is preferably 0.0001 wt %–1 wt %, more preferably 0.001 wt %–0.01 wt %, relative to citalopram hydrobromide used for crystallization.

In (A1) in Method 1, citalopram hydrobromide is dissolved in a specific solvent preferably by heating to 50° C.–80° C., more preferably 55° C.–75° C.

The specific solvent used in Method 1 contains at least one member selected from the group consisting of alcohol having 1 to 3 carbon atoms (e.g., methanol, ethanol, isopropyl alcohol, 1-propanol), water and acetone, in a proportion of preferably not less than 70 wt %, more preferably not less than 80 wt %. The solvent that may be contained in addition to alcohol having 1 to 3 carbon atoms, water and acetone is not subject to any particular limitation, and may be any as long as it is miscible with these solvents and is not reactive with citalopram hydrobromide. Examples thereof include toluene, xylene, tetrahydrofuran, diisopropyl ether, 1,2-dimethoxyethane, diethylene glycol dimethyl ether and the like. These may be used alone or in a combination of 2 or more solvents, wherein the boiling point thereof is preferably higher than the above-mentioned heating temperature. More preferable examples of the above-mentioned specific solvent include those containing at least one member selected from the group consisting of methanol, ethanol, isopropyl alcohol and 1-propanol in a proportion of not less than 80 wt %, particularly preferably those containing methanol and isopropyl alcohol in a proportion of not less than 90 wt %.

The amount of the above-mentioned specific solvent varies depending on the kind of each solvent used solely or in combination, the temperature at which citalopram hydrobromide is heated for dissolution and the like. However, it is generally preferably 2 L–30 L, more preferably 4 L–16 L, per 1 kg of citalopram hydrobromide. When a mixed solvent containing methanol and isopropyl alcohol is used, it is particularly preferable that the amounts thereof be 2 L–5 L of methanol and 4 L–8 L of isopropyl alcohol, both per 1 kg of citalopram hydrobromide.

According to Method 1, after the completion of step 2, the crystallization of citalopram hydrobromide is preferably completed after aging at a temperature below the final cooling temperature (preferably −10° C. to 30° C., more preferably 0° C. to 20° C.) for preferably 30 minutes–48 hours, more preferably 2 hours–24 hours, to achieve an improved yield.

By the foregoing steps, the characteristics of citalopram hydrobromide crystals can be controlled. For example, to shift the particle size distribution of the crystals toward that of the crystals having a greater particle size, the cooling rate may be slowed or a seed crystal may be added in (B1). To increase the aspect ratio, the cooling rate or the stirring speed may be slowed in (B1).

Method 2

The second method for crystallizing citalopram hydrobromide according to the present invention includes the steps of:

(A2) dissolving citalopram hydrobromide in a specific solvent by heating, (B2) crystallizing citalopram hydrobromide by cooling the obtained solution, (C2) heating the resulting crystals to dissolve a part of the obtained crystals, and (D2) recrystallizing citalopram hydrobromide while controlling a cooling rate (hereinafter this method is to be referred to as Method 2). The crystals obtained in Method 2 generally contain fine crystals in a smaller proportion than in Method 1. In Method 2, the steps of (A2) to (D2) can be performed in one pot. In each step, it is preferable that the particles be stirred at 10 rpm–250 rpm, particularly at 50 rpm–220 rpm, so that the temperature of the system as a whole will be uniform and the crystals after stirring will not have a smaller aspect ratio.

In Method 2, the control of the cooling rate of the solution within the specific temperature range in (D2) is particularly important for the control of the crystal characteristics. That is, the present inventors have found that the cooling rate of the solution particularly within the temperature range of from (heating temperature in (C2)) to (this heating temperature −30° C.) in (D2) in Method 2 affects the crystal particle size of the ultimate crystals. For example, the crystals obtained when the average cooling rate of the solution within this temperature range is controlled to not less than 30° C./hour and not more than 90° C./hour contain crystals having a particle size of less than 5 μm in a proportion of 35% at most, particularly not more than 25%, and have an average particle size of about 10 μm–25 μm. The crystals obtained when it is controlled to not less than 1° C./hour and less than 30° C./hour contain crystals having a particle size of less than 5 μm in a proportion of 35% at most, particularly not more than 15%, and have an average particle size of about 15 μm–30 μm. Cooling within the above-mentioned temperature range is preferably conducted such that the cooling rate becomes almost constant.

A next important process for controlling the crystal characteristics is the addition of a seed crystal within the specific temperature range in (B2) and dissolution by heating in (C2).

In (B2), the solution obtained in (A2) is cooled to the temperature range of preferably not less than 30° C. and less than 48° C., particularly preferably not less than 40° C. and less than 48° C. The present inventors have found that, in (B2), cooling to the temperature range of preferably not less than 30° C. and less than 48° C., particularly preferably not less than 40° C. and less than 48° C., which is followed by addition of a seed crystal to allow for crystallization results in the precipitation of crystals suitably grown. Thus, the particle size of the crystals can be controlled well, and generation of fine crystals having a particle size of less than 5 μm can be further inhibited.

When the temperature at which a seed crystal is added is less than 30° C., crystallization occurs at once and fine crystals tend to increase. When it is not less than 48° C., the seed crystal tends to dissolve easily, and the effect of the addition of the seed crystal becomes low. The amount of the seed crystal added is not subject to any particular limitation, but it is preferably 0.0001 wt %–1 wt %, more preferably 0.001 wt %–0.01 wt %, relative to citalopram hydrobromide used for crystallization.

In (C2), a part of the crystals obtained in (B2) is dissolved by heating, thereby preventing complete dissolution of the obtained crystals. This has a consequence that the finally obtained crystals have a greater average particle size. This is considered to be attributable to the fact that the crystals not dissolved by heating in (B2) become the seed crystal in (D2). Therefore, combined with the addition of the seed crystal in (B2), crystals having a greater average particle size as compared to that obtained without such combination can be ultimately obtained. As used herein, the "part of the crystals obtained in (B2)" is not subject to any particular limitation, but it is preferably 10 wt %–90 wt %, more preferably 20 wt %–80 wt %, of the crystals obtained in (B2).

The temperature in (C2) is not subject to any particular limitation as long as it can dissolve only a part of the crystals obtained in (B2). Note that the crystals should not be dissolved completely in (B2). It is preferable that a part of the crystals be dissolved by heating to not less than 48° C. and not more than 60° C., particularly not less than 48° C. and not more than 55° C. When this temperature is less than 48° C., the crystals cannot be dissolved to the desired degree in this step, and when it exceeds 60° C., the crystals are dissolved to the degree beyond the intended degree in this step, both causing an increase in the content of the crystals having a particle size of less than 5 μm, as compared to (C2) performed in the above-mentioned temperature range.

In Method 2, the cooling rate controlled in (B2) also affects the particle size of the final crystals, as is the case with the aforementioned control of cooling rate in (D2), only to a smaller degree than in (D2). In (B2), the present inventors have found that the cooling rate within the temperature range of preferably 0° C.–80° C., particularly 20° C.–40° C., affects the crystal particle size of citalopram hydrobromide. The cooling in the above-mentioned temperature range is preferably performed such that the cooling rate becomes almost the same.

In (A2) in Method 2, citalopram hydrobromide is dissolved in a specific solvent preferably by heating to 50° C.–80° C., more preferably 55° C.–75° C.

The specific solvent used in Method 2 contains at least one member selected from the group consisting of alcohol having 1 to 3 carbon atoms (e.g., methanol, ethanol, isopropyl alcohol, 1-propanol), water and acetone, preferably in a proportion of not less than 70 wt %, more preferably not less than 80 wt %. The solvent that may be contained in addition to alcohol having 1 to 3 carbon atoms, water and acetone is not subject to any particular limitation, and may be any as long as it is miscible with these solvents and is not reactive with citalopram hydrobromide. Examples thereof include toluene, xylene, tetrahydrofuran, diisopropyl ether, 1,2-dimethoxyethane, diethylene glycol dimethyl ether and the like. These may be used alone or in a combination of 2 or more solvents, wherein the boiling point thereof is preferably higher than the above-mentioned heating temperature. More preferable examples of the above-mentioned specific solvent include those containing at least one member selected from the group consisting of methanol, ethanol, isopropyl alcohol and 1-propanol in a proportion of not less than 80 wt %. Those containing methanol and isopropyl alcohol in a proportion of not less than 90 wt % are particularly preferable.

The amount of the above-mentioned specific solvent varies depending on the kind of each solvent used solely or in combination, the temperature at which citalopram hydrobromide is heated for dissolution and the like. However, it is generally preferably 2 L–30 L, more preferably 4 L–16 L, per 1 kg of citalopram hydrobromide. When a mixed solvent containing methanol and isopropyl alcohol is used, it is particularly preferable that the amounts thereof be 2 L–5 L of methanol and 4 L–8 L of isopropyl alcohol, both per 1 kg of citalopram hydrobromide.

In Method 2, (C2) and (D2) may be sequentially repeated after (D2). The crystallization of citalopram hydrobromide is preferably completed after aging at a temperature below the final cooling temperature (preferably –10° C. to 30° C., more preferably 0° C. to 20° C.) for preferably 30 minutes–48 hours, more preferably 2 hours–24 hours, to achieve an improved yield.

By the foregoing steps, the characteristics of citalopram hydrobromide crystals can be controlled. For example, to shift the particle size distribution of the crystals toward that of the crystals having a greater particle size, the cooling rate may be slowed in (B2) and (D2), a seed crystal may be added in (B2), and the crystals may be heated for dissolution at a specific temperature in (C2). To increase the aspect ratio, the cooling rate or the stirring speed may be slowed in (B2) and (D2).

In Method 1 and Method 2, the obtained crystals are isolated and purified by conventional methods, such as washing with a suitable solvent after filtration.

The citalopram hydrobromide crystals wherein 35% at most, preferably not more than 30%, more preferably not more than 20%, thereof has a crystal particle size of less than 5 μm, and further the crystals wherein not less than 10%, more preferably not less than 20%, thereof preferably has a particle size of not less than 20 μm, can improve the filterability after crystallization for the production of pharmaceutical bulk and the like. In addition, they can improve the problems of scattering of fine particles and exposure of the workers to the fine particles during production of a pharmaceutical preparation, and the like. These crystals can be obtained by each method as follows.

In Method 1, the average cooling rate of the solution within the temperature range of from 20° C. to 40° C. in (B1) is controlled to not less than 0.5° C./hour and not more than 60° C./hour, preferably by adding a seed crystal at a temperature range of not less than 30° C. and less than 48° C. in (B1).

In Method 2, the cooling rate of the solution in the temperature range of from ((heating temperature in (C2)) to (this heating temperature—30° C.) in (D2) is controlled to not less than 1° C./hour and not more than 90° C./hour, or preferably a seed crystal is added at a temperature range of not less than 30° C. and less than 48° C. in (B2), or a part of the obtained crystals in (B2) is heated for dissolution in (C2).

The citalopram hydrobromide crystals having an average aspect ratio of generally not less than 2.0, preferably not less than 3, and more preferably not less than 4.5, and generally not more than 9.0, preferably not more than 7, and more preferably not more than 6.0, can improve the problems such as poor filtering performance after crystallization for the preparation of a pharmaceutical bulk and poor fluidity when crystals are being taken out, and can be advantageously used for the production of citalopram hydrobromide and the production of pharmaceutical products. From this viewpoint, the crystals having an average aspect ratio of not less than 4.5 and not more than 6.0 are particularly preferable. These crystals can be obtained by each method as follows.

In Method 1, the average cooling rate of the solution in the temperature range of 20° C.–40° C. in (B1) is controlled to not less than 0.5° C./hour and not more than 60° C./hour, and preferably the stirring speed is set for 10 rpm–250 rpm in (B1). In (B1), the speed at the tip of an agitation part is generally set to 0.1 m/s–2.5 m/s, preferably 0.5 m/s–2.0 m/s.

In Method 2, the cooling rate of the solution within the temperature range of from (heating temperature in (C2)) to (this heating temperature—30° C.) is controlled to not less than 1° C./hour and not more than 90° C./hour in (D2), and preferably the stirring speed is set for 10 rpm–250 rpm in (B2) and (D2). In (B2) and (D2), the speed at the tip of an agitation part is generally set to 0.1 m/s–2.5 m/s, preferably 0.5 m/s–2.0 m/s.

By setting the speed at the tip of an agitation part to generally from not less than 2.5 m/s to less than 5.0 m/s, preferably from not less than 3.0 m/s to not more than 4.0 m/s, in (B1) in Method 1 and (B2) and (D2) in Method 2, crystals having an average aspect ratio of not less than 2.5 and less than 4.5 can be obtained. The crystals having an average aspect ratio of not less than 2.5 and less than 4.5 are preferable because they can be used as they are as a pharmaceutical preparation.

The citalopram hydrobromide to be used may be any that can be obtained by any method. It is preferably purified by active charcoal and the like before being subjected to the crystallization according to the present invention. The citalopram hydrobromide can be obtained, for example, according to the disclosure in, for example, U.S. Pat. No. 4,650,884.

The present invention is explained in more detail in the following by referring to Examples that do not limit the present invention in any way.

The powder X-ray crystal diffraction and average particle size were measured in the following Reference Example, Examples and Comparative Example, according to the following methods.

Powder X-ray crystal diffraction: Rigaku Corporation MiniFlex Irradiated X-ray CuKa Average particle size: SHIMADZU CORPORATION SALD1100 (medium:diisopropyl ether)

REFERENCE EXAMPLE 1

Citalopram base (167 g) was dissolved in acetone (837 ml). Thereto was blown in a hydrobromic acid gas at 15° C.–40° C. to make the pH of the solution 3. When about ½ of the hydrobromic acid gas was blown in, crystals began to precipitate. The reaction mixture was stirred at 25° C.–35° C. for 1 hour, and at 0° C.–5° C. for 1 hour. The resulting crystals were filtered, washed with cold acetone (167 ml) and dried in vacuo at 50° C.–70° C. (5 Torr–30 Torr) for 3 hours to give citalopram hydrobromide crystals (162 g). The crystals had an HPLC purity of 97.3% (254 nm).

melting point 180.3° C.

$^1$H-NMR (DMSO-$d_6$, 400 MHz): shown in FIG. 1.

Figure 2:
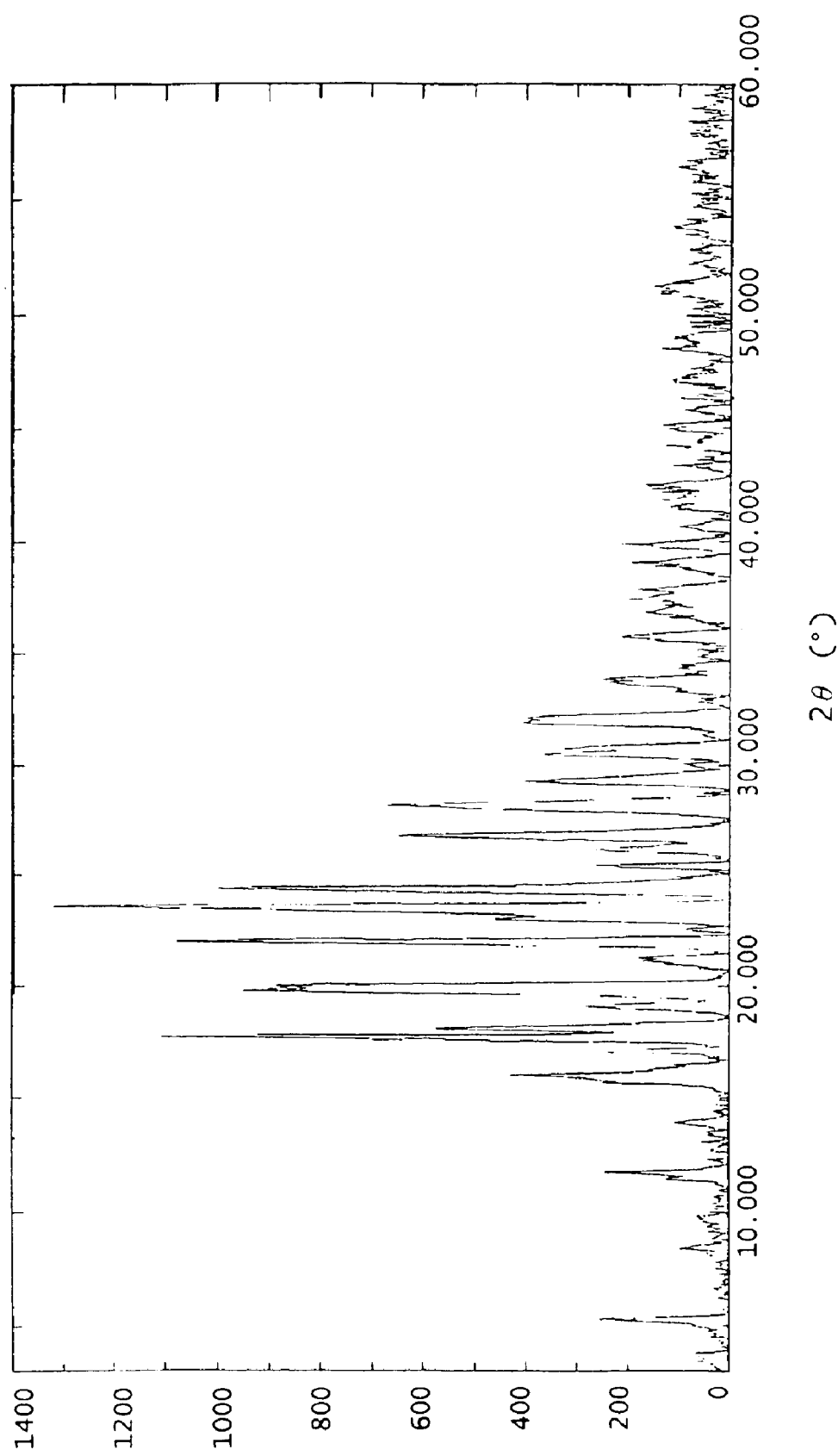
FIG. 2 shows a powder X-ray crystal diffraction pattern of the compound obtained in Reference Example 1.

Powder X-ray crystal diffraction pattern: shown in FIG. 2.

EXAMPLE 1

Citalopram hydrobromide (5.0 g) was synthesized according to Reference Example 1 and dissolved in methanol (15 ml) at 60° C. Thereto was added active charcoal (0.5 g) and the mixture was stirred for 15 minutes. The active charcoal was filtered off and isopropyl alcohol (25 ml) was added. The mixture was heated to 58° C. to dissolve the crystals. When the mixture was cooled to 43° C. while stirring at 200 rpm (propeller diameter: 0.05 m, speed at the tip of propeller: 0.05×(200/6)×3.14=ca. 0.5 m/s), the seed crystal (about 0.1 mg) of citalopram hydrobromide was added. The mixture was cooled to 40° C. over 15 minutes and then cooled from 40° C. to 20° C. over 5 hours while stirring at 200 rpm to make the cooling rate almost the same (average cooling rate: 4° C./hour). The cooled suspension was stirred at 20° C. for 18 hours (retention time at 20° C.) at 200 rpm and the resulting crystals were filtered. The crystals were dried at 50° C. (0.67 kPa–1.33 kPa) for 3 hours in vacuo while stirring them at 30 rpm, and stood for drying at 70° C. (0.4 kPa–0.8 kPa) for 15 hours.

Figure 3:
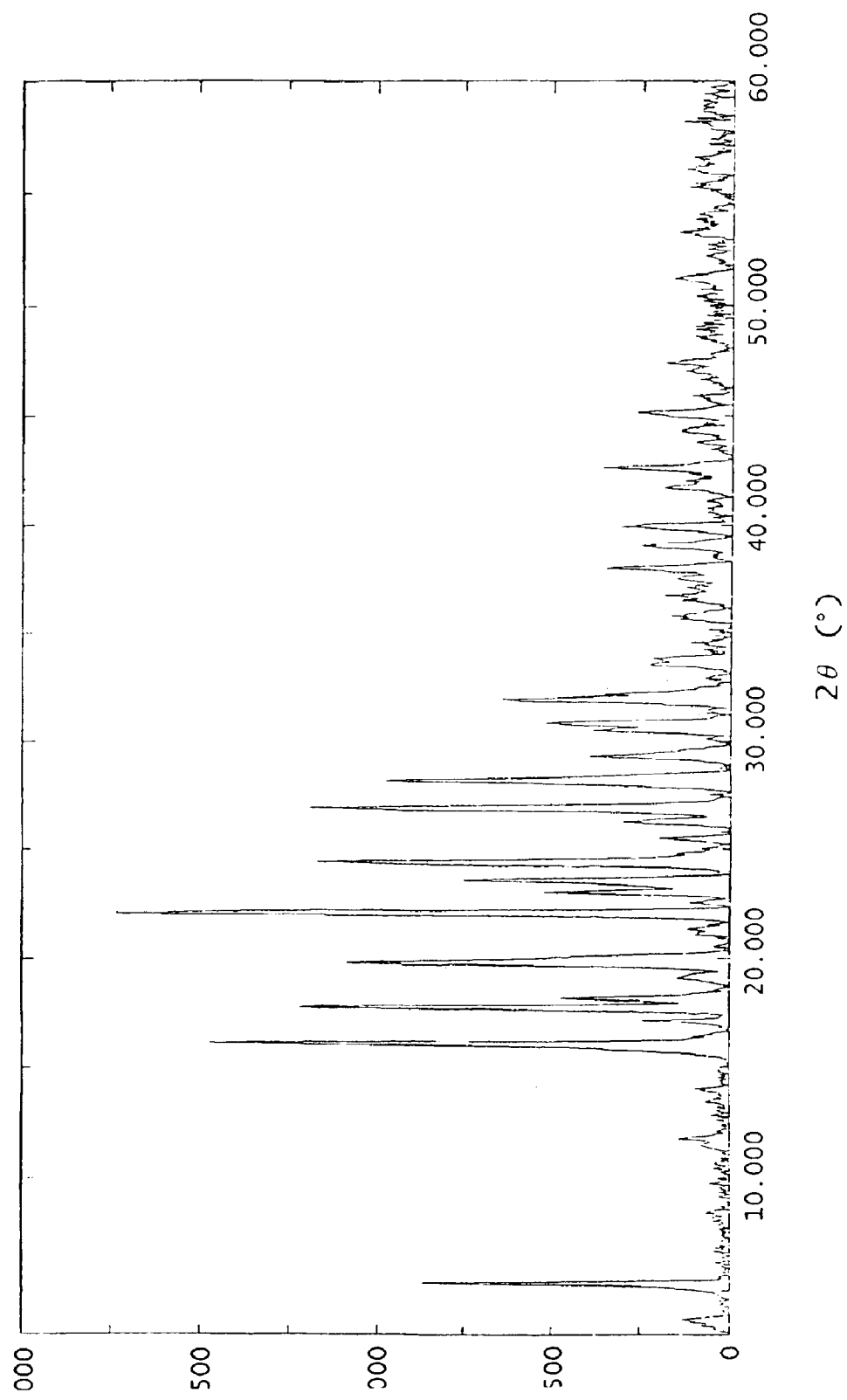
FIG. 3 shows a powder X-ray crystal diffraction pattern of the compound obtained in Example 1.
Figure 6:
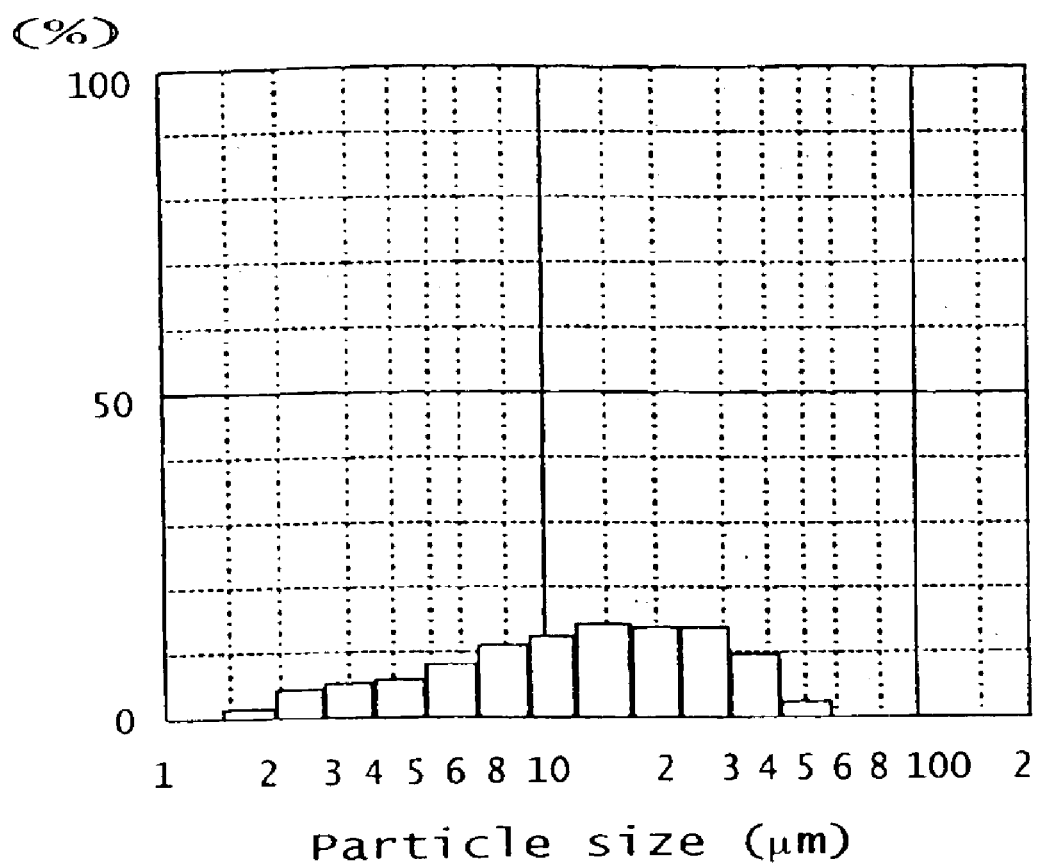
FIG. 6 shows a crystal particle size distribution of the compound obtained in Example 1.
Figure 13:
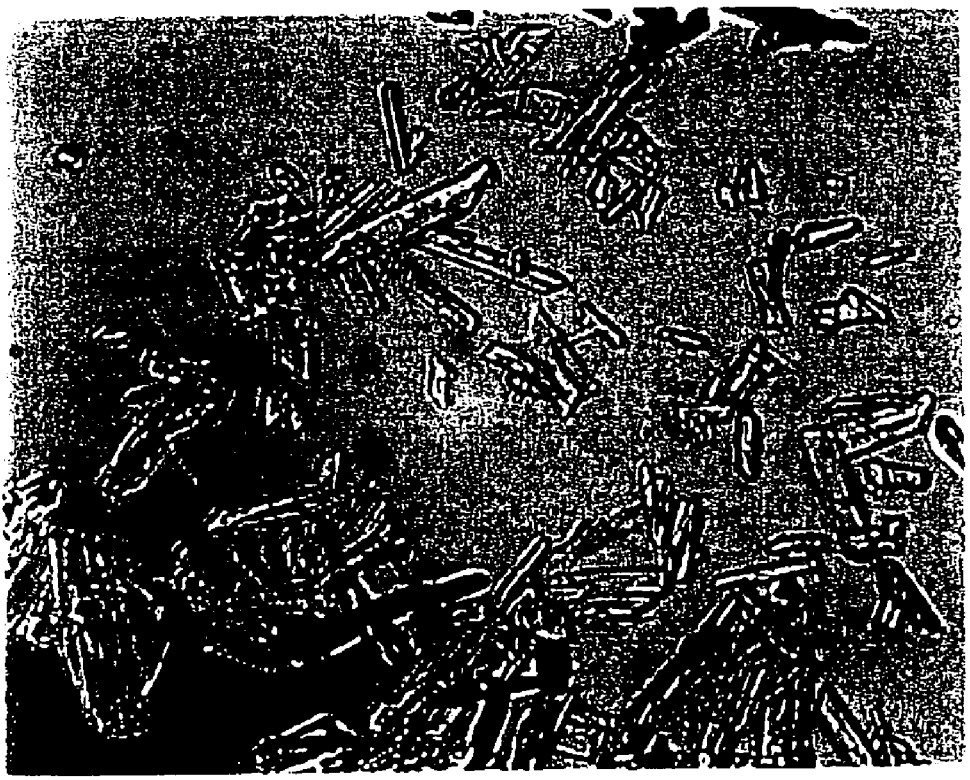
FIG. 13 shows a micrograph (400 magnifications) of the compound obtained in Example 1.

The obtained citalopram hydrobromide crystals weighed 4.2 g, and the crystals had a melting point of 184.4° C. and an HPLC purity of 99.9% (254 nm).

powder X-ray crystal diffraction pattern: shown in FIG. 3
crystal particle size distribution
less than 5 μm 17.1%,
not less than 5 μm and less than 10 μm 22.2%,
not less than 10 μm and less than 20 μm 29.1%,
not less than 20 μm and less than 40 μm 27.0%,
not less than 40 μm 4.6% (shown in FIG. 6)
average particle size 12.9 μm
micrograph (400 magnifications): shown in FIG. 13
average aspect ratio: 4.8

EXAMPLES 2–3

The procedure followed Example 1 except that the cooling time of from 40° C. to 20° C. and the retention time at 20° C. were changed to those shown in Table 1.

TABLE 1

Figure 7:
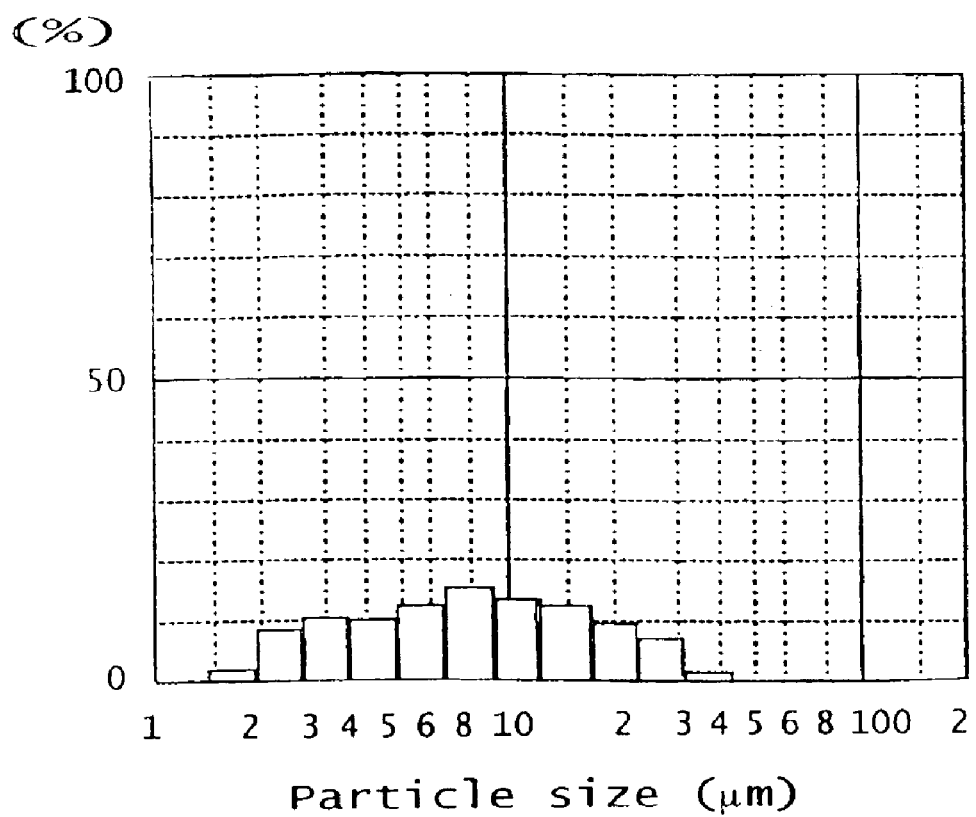
FIG. 7 shows a crystal particle size distribution of the compound obtained in Example 2.
Figure 8:
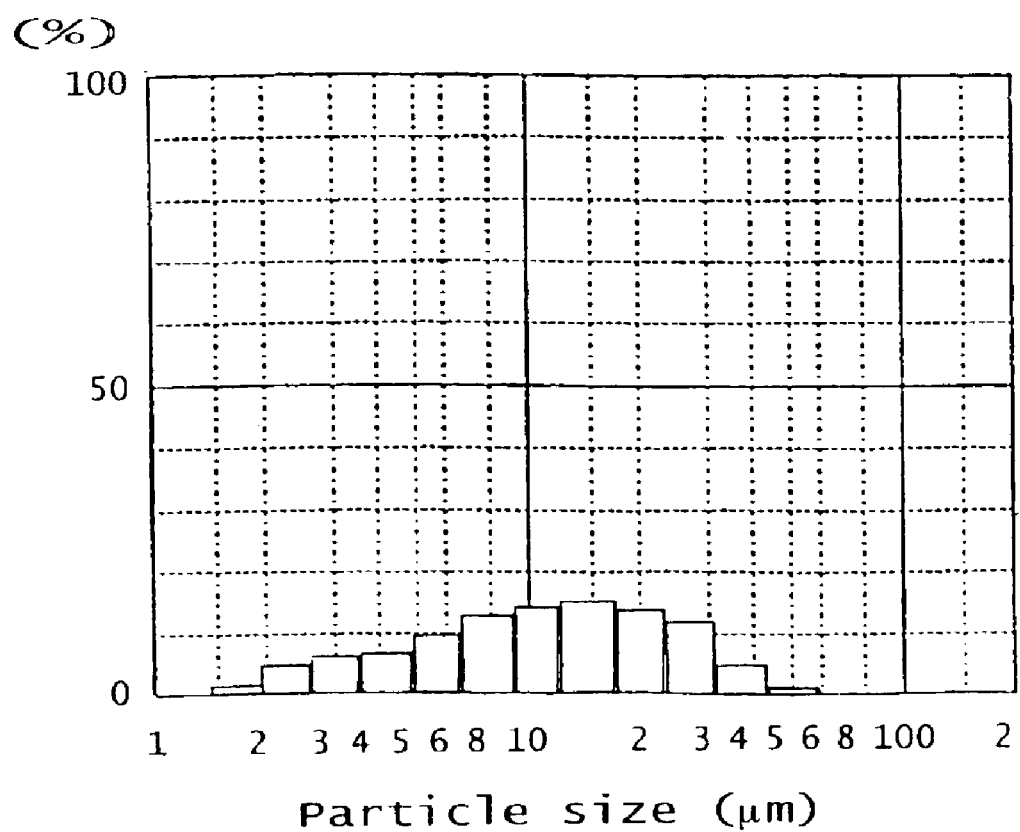
FIG. 8 shows a crystal particle size distribution of the compound obtained in Example 3.

| Ex. | Cooling time of from 40° C. to 20° C. (cooling rate in parenthesis) | Retention time at 20° C. | Crystal particle size distribution (D) | Average particle size (μm) |
|---|---|---|---|---|
| 2 | 30 min (40° C./hour) | 19 hr 30 min | D < 5 μm 31.4%<br>5 μm ≦ D < 10 μm 30.3%<br>10 μm ≦ D < 20 μm 25.7%<br>20 μm ≦ D < 40 μm 12.2%<br>D ≧ 40 μm 0.3%<br>(shown in FIG. 7) | 7.8 |
| 3 | 1 hr (20° C./hour) | 19 hr | D < 5 μm 19.6%<br>5 μm ≦ D < 10 μm 26.0%<br>10 μm ≦ D < 20 μm 31.0%<br>20 μm ≦ D < 40 μm 21.6%<br>D ≧ 40 μm 1.6%<br>(shown in FIG. 8) | 11.0 |

EXAMPLE 4

Citalopram hydrobromide (5.0 g) was synthesized according to Reference Example 1 and dissolved in methanol (15 ml) at 50° C. Thereto was added active charcoal (0.5 g) and the mixture was stirred for 15 minutes. The active charcoal was filtered off and isopropyl alcohol (25 ml) was added. The mixture was heated to 58° C. to dissolve the crystals. When the mixture was cooled to 43° C. while stirring at 200 rpm (propeller diameter: 0.05 m), the seed crystal (0.1 mg) of citalopram hydrobromide was added. The mixture was cooled to 41° C. over 15 minutes and heated to 50° C. over 5 minutes, and then stirred at the same temperature for 80 minutes to allow dissolution of a part of the crystals (about half). Then, the mixture was cooled from 50° C. to 20° C. over 2.5 hours to make the cooling rate almost the same (average cooling rate: 12° C./hour). The cooled suspension was stirred at 20° C. for 17.5 hours at 200 rpm and the precipitated crystals were filtrated. The crystals were dried at 50° C. (0.67 kPa–1.33 kPa) for 3 hours in vacuo with stirring at 30 rpm, and stood for drying at 70° C. (0.4 kPa–0.8 kPa) for 15 hours.

Figure 4:
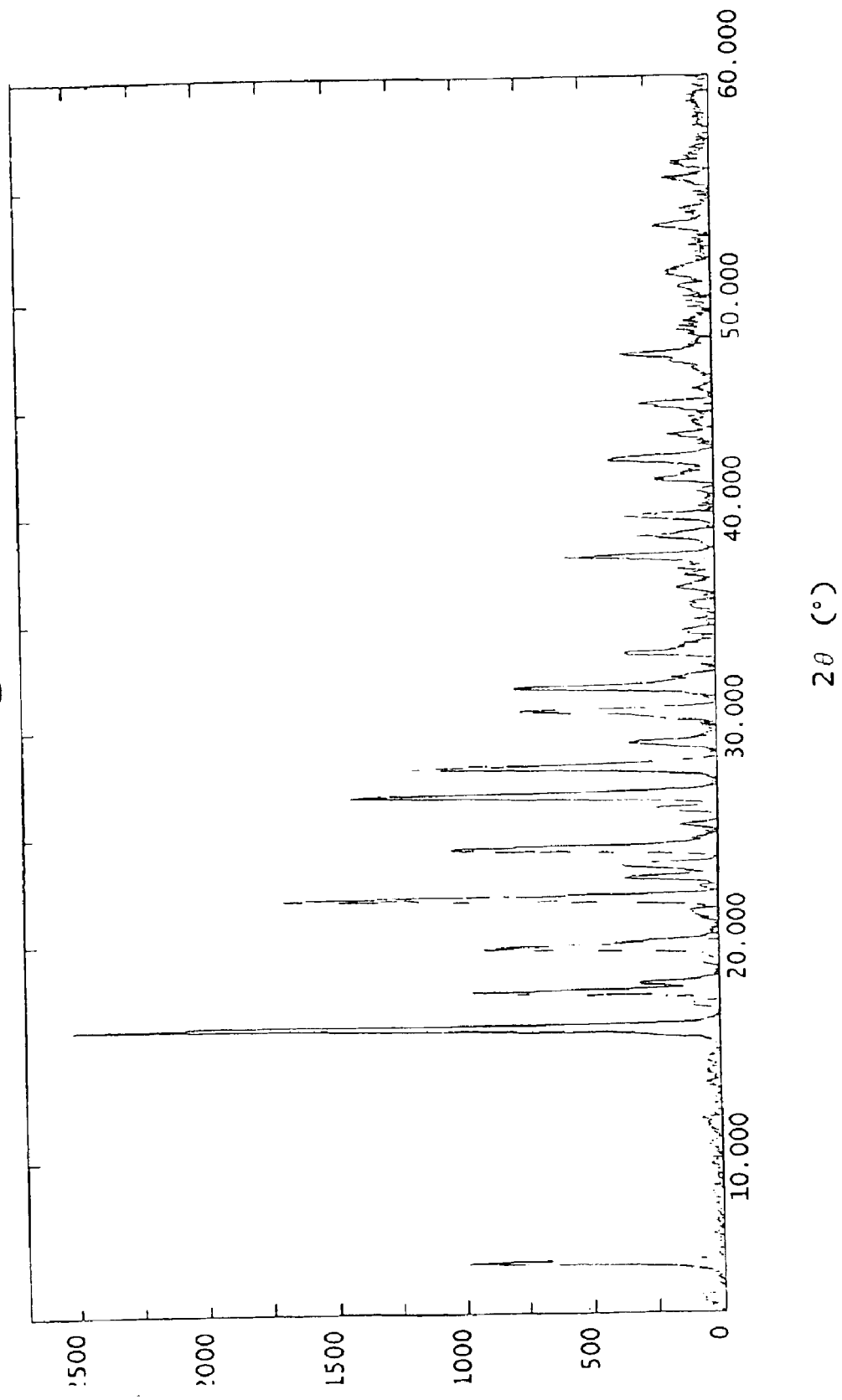
FIG. 4 shows a powder X-ray crystal diffraction pattern of the compound obtained in Example 4.
Figure 9:
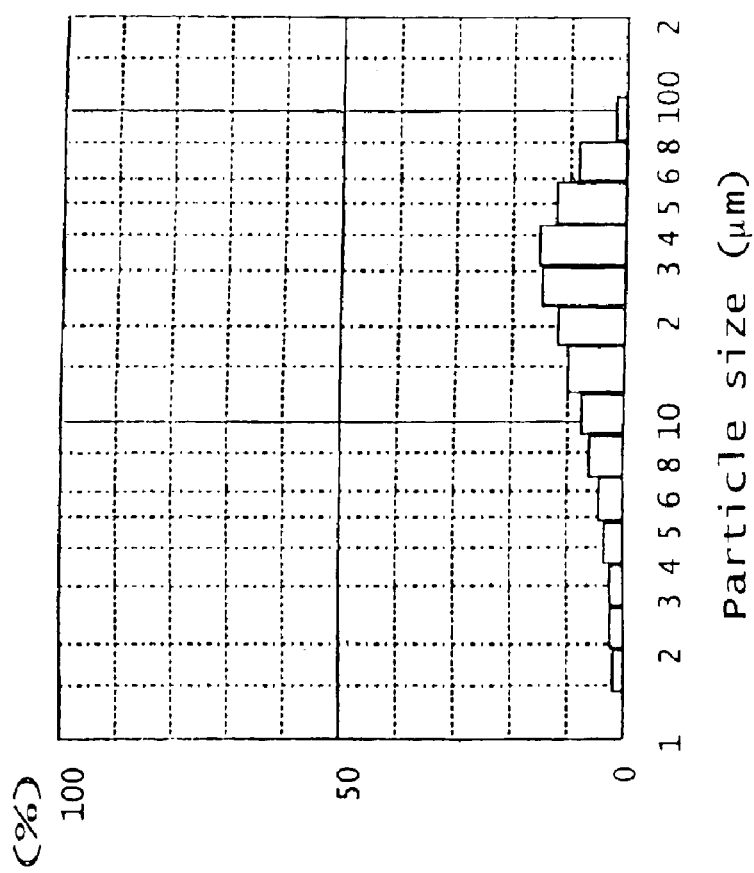
FIG. 9 shows a crystal particle size distribution of the compound obtained in Example 4.
Figure 14:
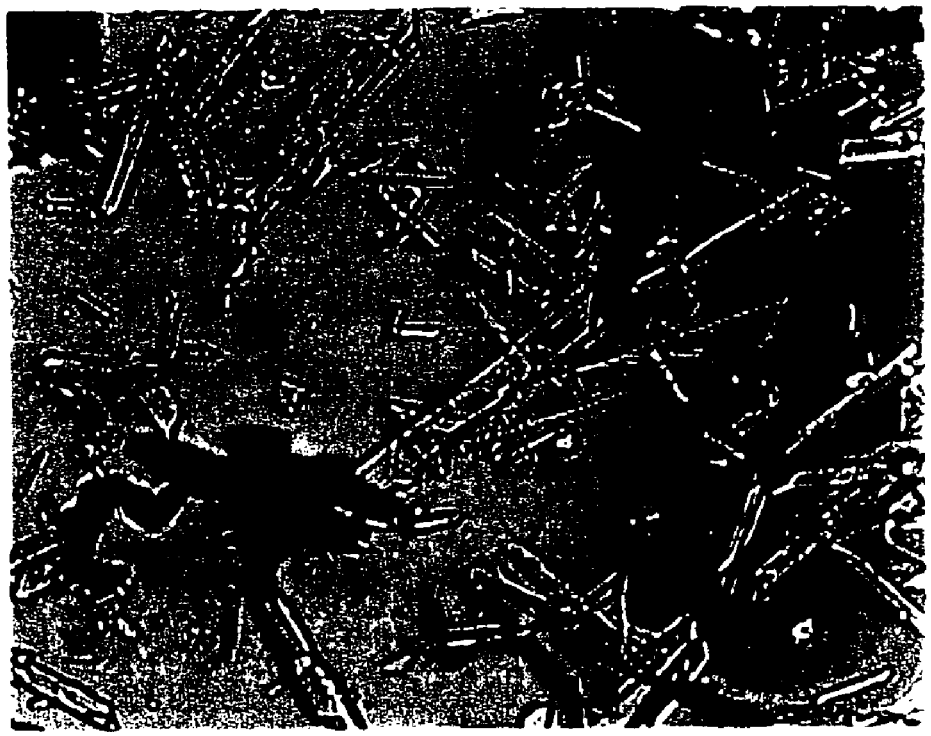
FIG. 14 shows a micrograph (400 magnifications) of the compound obtained in Example 4.

The obtained citalopram hydrobromide crystals weighed 4.1 g and the crystals had an HPLC purity of 99.9% (254 nm) and a melting point of 184.7° C.

powder X-ray crystal diffraction pattern: shown in FIG. 4.
crystal particle size distribution
less than 5 μm 9.6%,
not less than 5 μm and less than 10 μm 12.3%,
not less than 10 μm and less than 20 μm 20.9%,
not less than 20 μm and less than 40 μm 31.7%,
not less than 40 μm 25.5% (shown in FIG. 9)
average particle size 23.8 μm
micrograph (400 magnifications): shown in FIG. 14
average aspect ratio: 5.4

EXAMPLE 5

The procedure followed Example 4 except that the cooling time of from 50° C. to 20° C. and the retention time at 20° C. were changed to those shown in Table 2.

TABLE 2

Figure 10:
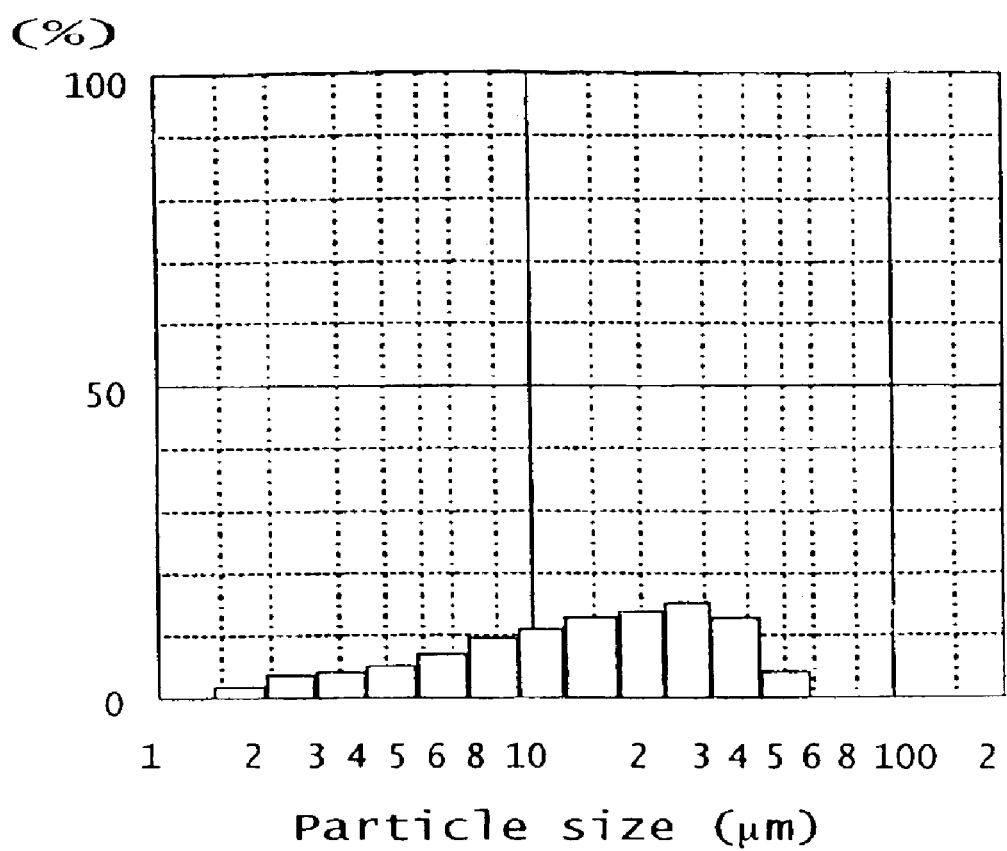
FIG. 10 shows a crystal particle size distribution of the compound obtained in Example 5.

| Ex. | Cooling time of from 50° C. to 20° C. (cooling rate in parenthesis) | Retention time at 20° C. | Crystal particle size distribution (D) | Average particle size (μm) |
|---|---|---|---|---|
| 5 | 30 min (60° C./hr) | 19 hr 30 min | D < 5 μm 15.6% <br> 5 μm ≤ D < 10 μm 19.3% <br> 10 μm ≤ D < 20 μm 26.9% <br> 20 μm ≤ D < 40 μm 31.0% <br> D ≥ 40 μm 7.2% (shown in FIG. 10) | 15.1 |

EXAMPLE 6

Citalopram hydrobromide (18.2 kg) was synthesized according to Reference Example 1 and dissolved in methanol (37.4 kg) at 45° C.–50° C. Thereto was added active charcoal (1.8 kg) and the mixture was stirred for 55 minutes. The active charcoal was filtered off and washed with warm methanol (7.2 kg). The washings and the filtrate were combined and heated to about 60° C. Isopropyl alcohol (71.9 kg) heated to 40° C.–50° C. was added, and upon confirmation of dissolution at 62° C., the mixture was cooled with stirring at 169 rpm (diameter of impeller of agitator (Pfaudler type): 0.45 m, speed at the tip of impeller of agitator: ca. 4.0 m/s). When the mixture was cooled to 44° C., the seed crystal (about 400 mg) of citalopram hydrobromide was added. Stirring at 40° C.–43° C. for 30 minutes enabled confirmation of the precipitation of the crystals at 41.5° C.

The mixture was cooled from 40° C. to 20° C. over 4 hours (average cooling rate: 5° C./hour), and further cooled to 10° C. over 3 hours. The suspension was stirred at 5° C.–10° C. at 80 rpm for 13 hours and the crystals were filtrated. A mixture of isopropyl alcohol (9.6 kg) and methanol (4.8 kg) was cooled to 0° C.–10° C. The crystals were washed with this mixture. The wet crystals (19.8 kg) were dried under reduced pressure (10 kPa–1.33 kPa), at 30° C.–50° C. for 10 hours, at 45° C.–55° C. for 5 hours, and at 70° C.–75° C. for 8 hours, with stirring at 30 rpm.

Figure 11:
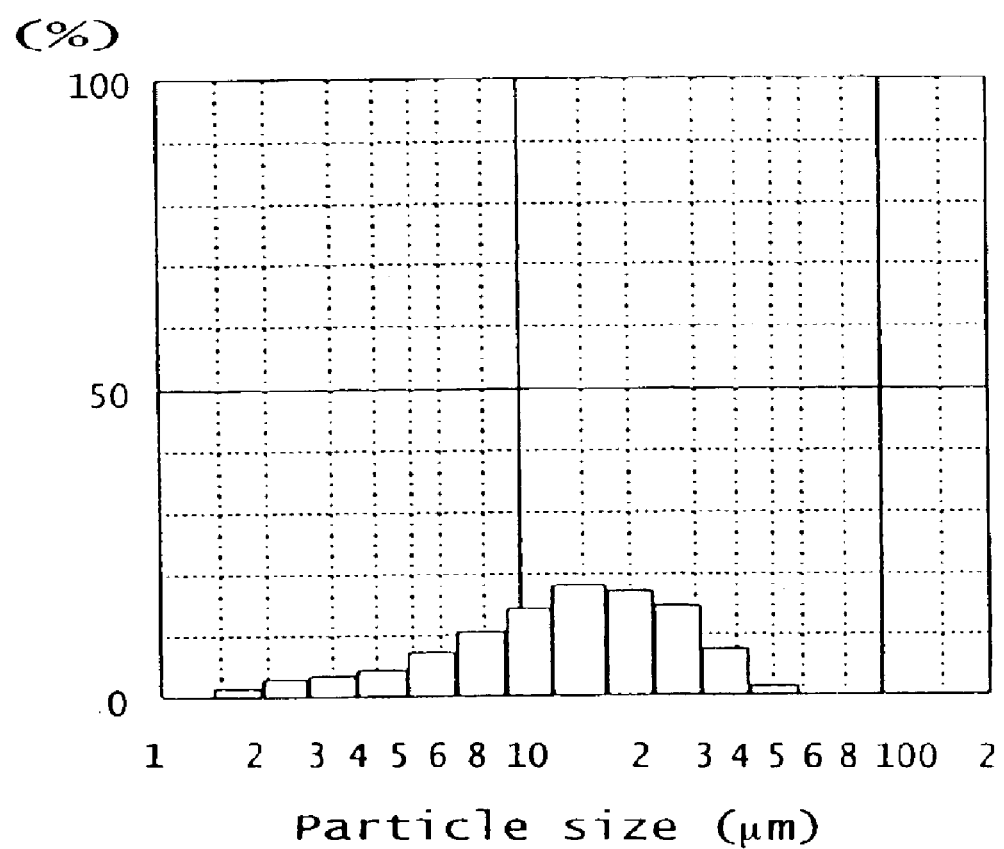
FIG. 11 shows a crystal particle size distribution of the compound obtained in Example 6.
Figure 15:
FIG. 15 shows a micrograph (400 magnifications) of the compound obtained in Example 6.

The obtained citalopram hydrobromide crystals weighed 15.0 kg (recrystallization yield : 82%) and the crystals had an HPLC purity of 99.75% (220 nm) and a melting point of 185.0° C.

crystal particle size distribution
  less than 5 μm 12.6%,
  not less than 5 μm and less than 10 μm 20.2%,
  not less than 10 μm and less than 20 μm 35.5%,
  not less than 20 μm and less than 40 μm 29.3%,
  not less than 40 μm 2.4% (shown in FIG. 11)
average particle size: 14.6 μm
micrograph (400 magnifications): shown in FIG. 15.
average aspect ratio: 3.0
bulk density: 0.2 g/ml
tap density 0.42 g/ml

COMPARATIVE EXAMPLE 1

Citalopram hydrobromide (5.0 g) was synthesized according to Reference Example 1 and dissolved in methanol (15 ml) at 50° C. Thereto was added active charcoal (0.5 g) and the mixture was stirred for 15 minutes. The active charcoal was filtered off and isopropyl alcohol (25 ml) was added. The mixture was heated to 58° C. to dissolve the crystals. The mixture was cooled to 40° C. over 5 min and then cooled from 40° C. to 20° C. over 5 min with stirring at 200 rpm. When the mixture was cooled to 20° C., the seed crystal (0.1 mg) was added. The mixture was stirred at the same temperature for 20 hours and the crystals were filtrated. The crystals were dried at 50° C. (0.67 kPa–1.33 kPa) for 3 hours in vacuo with stirring at 30 rpm, and stood for drying at 70° C. (0.4 kPa–0.8 kPa) for 15 hours.

Figure 5:
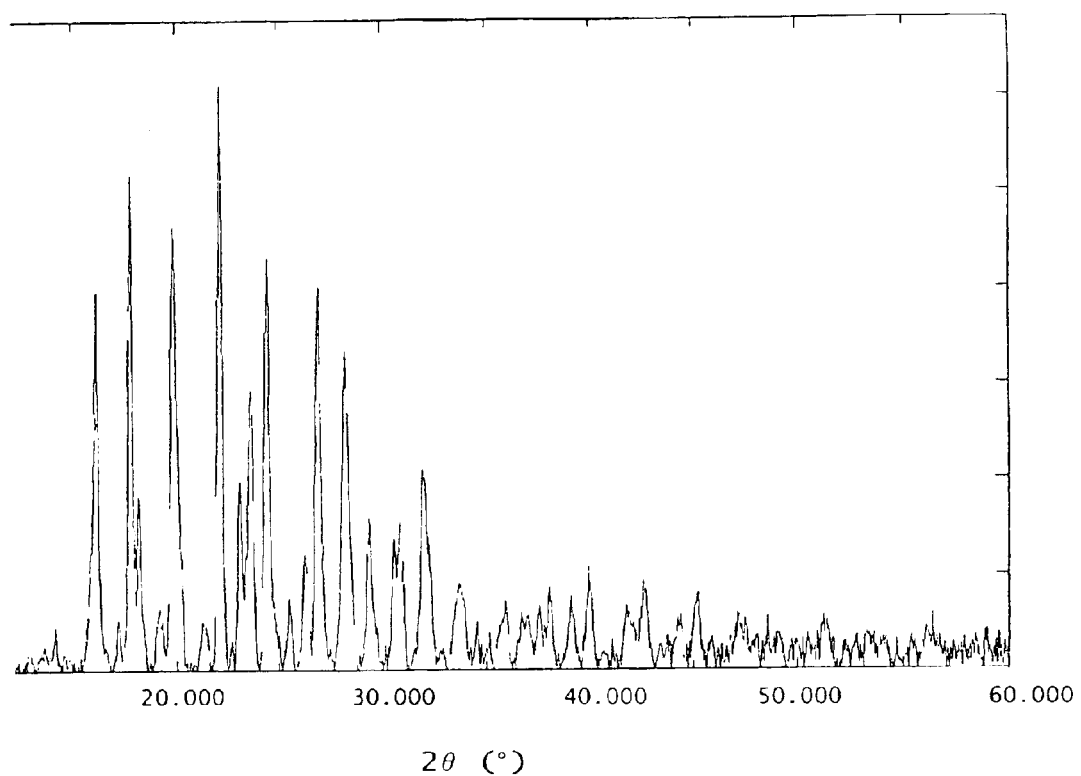
FIG. 5 shows a powder X-ray crystal diffraction pattern of the compound obtained in Comparative Example 1.
Figure 12:
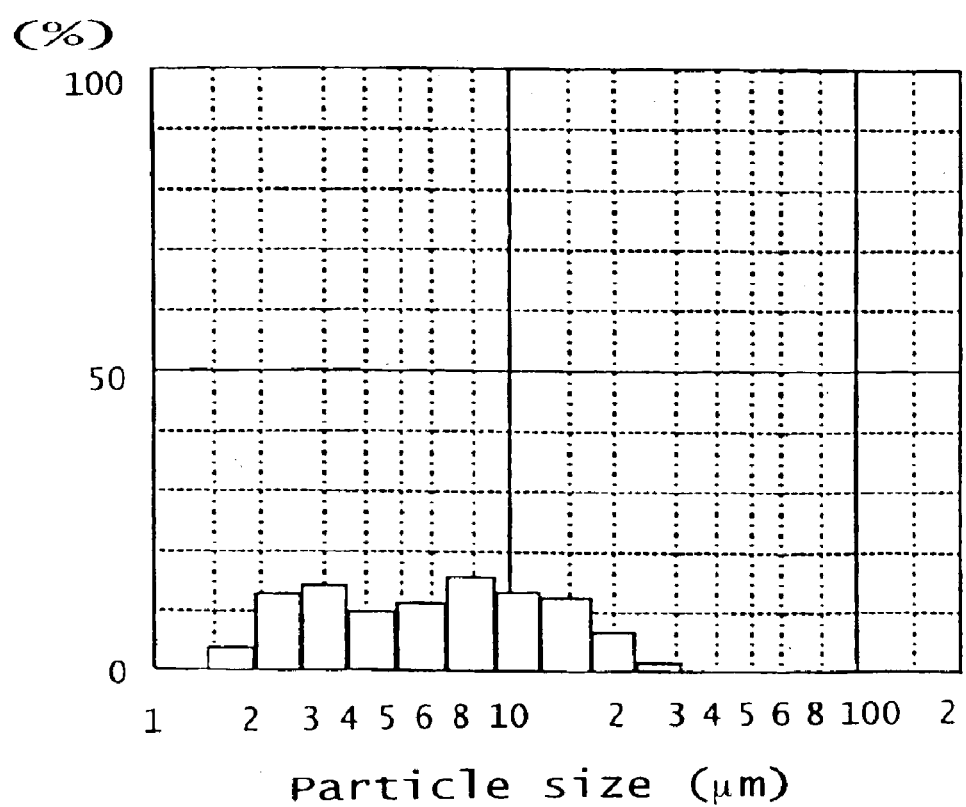
FIG. 12 shows a crystal particle size distribution of the compound obtained in Comparative Example 1.
Figure 16:
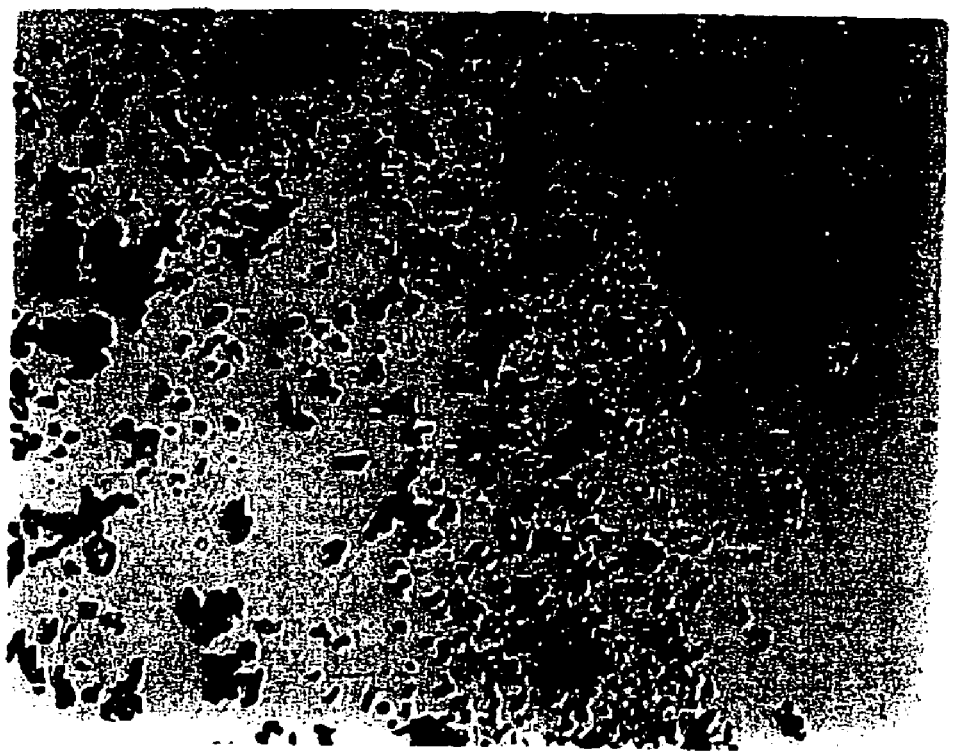
FIG. 16 shows a micrograph (400 magnifications) of the compound obtained in Comparative Example 1.
Figure 17:
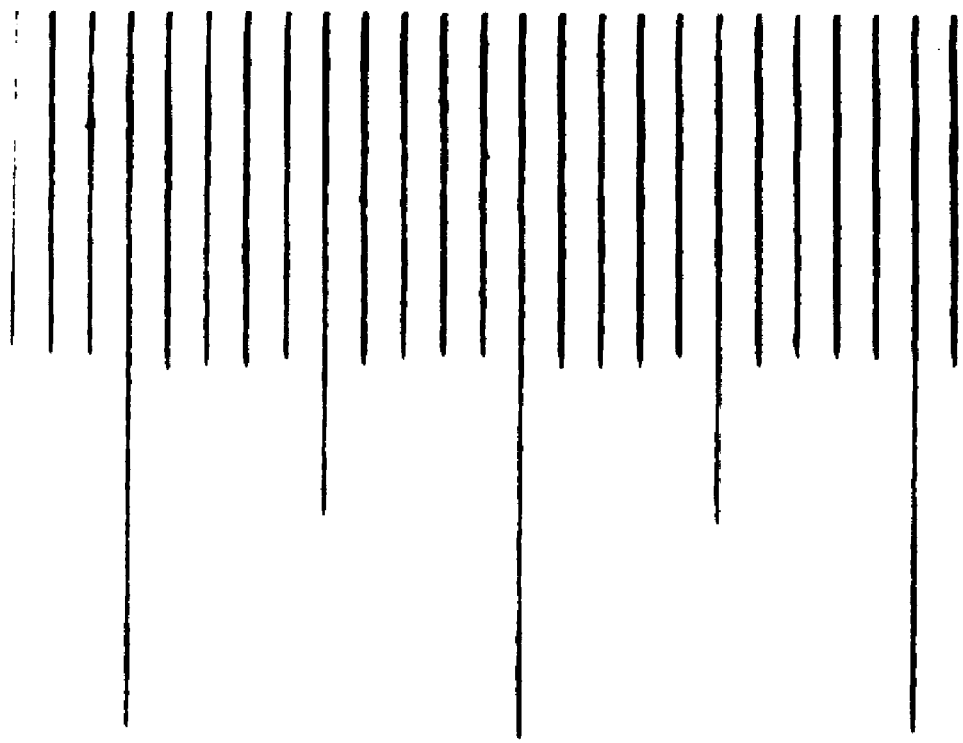
FIG. 17 shows a micrograph (400 magnifications) of a ruler graduated in 10 μm.

The obtained citalopram hydrobromide crystals weighed 4.3 g and the crystals had an HPLC purity of 99.9% (254 nm) and a melting point of 184.2° C.

powder X-ray crystal diffraction pattern: shown in FIG. 5
crystal particle size distribution
  less than 5 μm 41.9%,
  not less than 5 μm and less than 10 μm 30.2%,
  not less than 10 μm and less than 20 μm 23.9%,
  not less than 20 μm and less than 40 μm 4.0%,
  not less than 40 μm 0% (shown in FIG. 12)
average particle size: 6.3 μm
micrograph (400 magnifications): shown in FIG. 16

According to the method of the present invention, the crystal characteristics of citalopram hydrobromide, such as particle size, particle size distribution, aspect ratio and the like, can be controlled easily and industrially. In addition, citalopram hydrobromide crystals having crystal characteristics useful as a pharmaceutical bulk can be provided.

This application is based on application No. 2000-133995 filed in Japan, the contents of which are incorporated hereinto by reference.

What is claimed is:

1. Citalopram hydrobromide crystals having an average aspect ratio of not less than 2.0 and not more than 9.0.

2. The citalopram hydrobromide crystals of claim 1, which have an average aspect ratio of not less than 2.5 and less than 4.5.

3. The citalopram hydrobromide crystals of claim 1, which have an average aspect ratio of not less than 4.5 and not more than 6.0.

4. The citalopram hydrobromide crystals of claim 2, which contains crystals having a particle size of less than 5 μm in a proportion of 35% at most.

5. The citalopram hydrobromide crystals of claim 4, which comprise crystals having a particle size of not less than 20 μm in a proportion of not less than 10%.

6. The citalopram hydrobromide crystals of claim 3, which contains crystals having a particle size of less than 5 μm in a proportion of 35% at most.

7. The citalopram hydrobromide crystals of claim 6, which comprise crystals having a particle size of not less than 20 μm in a proportion of not less than 10%.

8. A method for crystallizing citalopram hydrobromide, which comprises the steps of (A1) dissolving, by heating, citalopram hydrobromide in a solvent comprising at least one member selected from the group consisting of alcohol having 1 to 3 carbon atoms, water and acetone and (B1) cooling the resulting product to allow for crystallization while controlling a cooling rate.

9. The method of claim 8, which comprises, after cooling to a temperature range of from not less than 30° C. to less than 48° C., adding a seed crystal of citalopram hydrobromide for crystallization.

10. The method of claim 8, which comprises controlling an average cooling rate of the solution in a temperature range of from 20° C. to 40° C. to not less than 0.5° C./hour and less than 30° C./hour.

11. The method of claim 10, which comprises, after cooling to a temperature range of from not less than 30° C. to less than 48° C., adding a seed crystal of citalopram hydrobromide for crystallization.

12. A method for crystallizing citalopram hydrobromide, which comprises the steps of
- (A2) dissolving, by heating, citalopram hydrobromide in a solvent comprising at least one member selected from the group consisting of alcohol having 1 to 3 carbon atoms, water and acetone,
- (B2) cooling the obtained solution to achieve crystallization,
- (C2) dissolving a part of the obtained crystals by heating, and
- (D2) recrystallizing while controlling a cooling rate.

13. The method according to claim 12, which comprises cooling to a temperature range of from not less than 30° C. to less than 48° C. in (B2).

14. The method according to claim 12, which comprises, after cooling to a temperature range of from not less than 30° C. to less than 48° C., adding a seed crystal of citalopram hydrobromide for crystallization in (B2).

15. The method according to claim 12, comprises dissolving a part of the crystals by heating to not less than 48° C. and not more than 60° C. in (C2).

16. The method according to claim 12, which comprises controlling the average cooling rate of the solution in the temperature range of from (heating temperature in (C2)) to (said heating temperature −30° C.) to not less than 30° C./hour and not more than 90° C./hour in (D2).

17. The method according to claim 12, which comprises controlling the average cooling rate of the solution in the temperature range of from (heating temperature in (C2)) to (said heating temperature −30° C.) to not less than 1° C./hour and less than 30° C./hour in (D2).

* * * * *

UNITED STATES PATENT AND TRADEMARK OFFICE
CERTIFICATE OF CORRECTION

| | | |
|---|---|---|
| PATENT NO. | : 6,977,306 B2 | Page 1 of 1 |
| DATED | : December 20, 2005 | |
| INVENTOR(S) | : Ikemoto et al. | |

It is certified that error appears in the above-identified patent and that said Letters Patent is hereby corrected as shown below:

<u>Column 14,</u>
Line 9, "comprises" should read -- which comprises --.

Signed and Sealed this

Twenty-fifth Day of April, 2006

JON W. DUDAS
*Director of the United States Patent and Trademark Office*